United States Patent
Skyba et al.

(10) Patent No.: US 6,692,438 B2
(45) Date of Patent: Feb. 17, 2004

(54) ULTRASONIC IMAGING SYSTEM AND METHOD FOR DISPLAYING TISSUE PERFUSION AND OTHER PARAMETERS VARYING WITH TIME

(75) Inventors: Danny M. Skyba, Bothell, WA (US); Damien Dolimier, Bothell, WA (US); Jeffry E. Powers, Bainbridge Island, WA (US)

(73) Assignee: Koninklijke Philips Electronics NV (NL)

( * ) Notice: Subject to any disclaimer, the term of this patent is extended or adjusted under 35 U.S.C. 154(b) by 174 days.

(21) Appl. No.: 10/025,200

(22) Filed: Dec. 18, 2001

(65) Prior Publication Data

US 2003/0114759 A1 Jun. 19, 2003

(51) Int. Cl.$^7$ ................................................ A61B 8/00
(52) U.S. Cl. ........................................ 600/440; 600/458
(58) Field of Search .............................. 600/440, 438, 600/458, 443, 437

(56) References Cited

U.S. PATENT DOCUMENTS

| | | | |
|---|---|---|---|
| 5,215,094 A | 6/1993 | Franklin et al. ....... 128/661.08 |
| 5,255,683 A | * 10/1993 | Monaghan .................. 600/458 |
| 5,474,073 A | 12/1995 | Schwartz et al. ......... 128/661.1 |
| 5,485,842 A | 1/1996 | Quistgaard ................ 128/66.07 |
| 5,706,819 A | * 1/1998 | Hwang et al. .............. 600/458 |
| 5,720,291 A | 2/1998 | Schwartz .................. 128/661.1 |
| 5,749,364 A | * 5/1998 | Sliwa et al. ................. 600/438 |
| 5,813,613 A | 9/1998 | Keenan et al. .............. 239/676 |
| 5,833,613 A | * 11/1998 | Averkiou et al. ........... 600/440 |
| 5,860,931 A | 1/1999 | Chandler .................... 600/458 |
| 6,171,246 B1 | 1/2001 | Averkiou et al. ........... 600/458 |
| 6,186,950 B1 | 2/2001 | Averkiou et al. ........... 600/443 |

\* cited by examiner

*Primary Examiner*—Marvin M. Lateef
*Assistant Examiner*—Ruby Jain
(74) *Attorney, Agent, or Firm*—Dorsey & Whitney LLP (57) ABSTRACT

A method and system for displaying a parametric image showing tissue perfusion includes an ultrasonic imaging system coupled to an ECG device. The ECG device triggers the imaging system to obtain contrast image data showing tissue perfusion at a respective predetermined time during each of a plurality of heartbeats. Parametric image data for discrete locations in the area of interest such as the myocardium is determined from the temporal contrast data acquired during reperfusion of the tissue in the area of interest. The parameters are mapped to a display value such as color to produce a parametric perfusion ultrasound image. Sequences of images may be produced which depict both perfusion characteristics and dynamic wall motion of the myocardium in a common image sequence.

24 Claims, 11 Drawing Sheets

| PIXEL X COORDINATE | PIXEL Y COORDINATE | PARAMETER VALUE A*B | COLOR VALUE |
|---|---|---|---|
| 100 | 100 | 19.7 | 200 |
| 100 | 101 | 21.0 | 210 |
| 100 | 102 | 19.7 | 200 |
| ... | ... | ... | ... |
| 175 | 157 | 1.3 | 10 |
| 175 | 158 | 1.7 | 17 |
| ... | ... | ... | ... |
| 203 | 50 | 2.3 | 19 |
| 203 | 51 | 2.7 | 21 |
| ... | ... | ... | ... |

ULTRASONIC IMAGING SYSTEM AND METHOD FOR DISPLAYING TISSUE PERFUSION AND OTHER PARAMETERS VARYING WITH TIME

TECHNICAL FIELD

This invention relates to diagnostic ultrasonic imaging, and, more particularly, to a system and method for displaying tissue perfusion and other time-varying parameters.

BACKGROUND OF THE INVENTION

Ultrasonic diagnostic imaging systems are capable of imaging and measuring the physiology within the body in a completely noninvasive manner. Ultrasonic waves are transmitted into the body from the surface of the skin and are reflected from tissue and cells within the body. The reflected echoes are received by an ultrasonic transducer and processed to produce an image or measurement of blood flow. Diagnosis is thereby possible with no invasion of the body of the patient.

Materials known as ultrasonic contrast agents can be introduced into the body to enhance ultrasonic diagnosis. Contrast agents are substances that strongly reflect ultrasonic waves, returning echoes which may be clearly distinguished from those returned by blood and tissue. One class of substances which has been found to be especially useful as an ultrasonic contrast agent is gases, in the form of tiny bubbles called microbubbles. Microbubbles strongly backscatter ultrasound in the body, thereby allowing tissues and blood containing the microbubbles to be readily detectable through special ultrasonic processing.

Although microbubbles can be simply very small bubbles of a suitable gas, microbubbles can also be very small bubbles of gas coated with a thin biodegradable coating or shell. These coated microbubbles typically have diameters between 0.1 and 4.0 microns and a specific density about $1/10$ of the density of water. Coated microbubbles are normally suspended in an aqueous solution for infusion into the blood stream. Coated microbubbles have the advantage of being stable in the body for a significant period of time, as the shells serve to protect the gases of the microbubbles from diffusion into the bloodstream. The size of the microbubbles may be chosen to enable the microbubbles to pass through capillary beds in the body. Therefore, microbubble contrast agents can be used for imaging the body's vascularized tissues, such as the walls of the heart, since the contrast agent can be injected into the bloodstream and will pass through veins, arteries and capillaries with the blood supply until filtered from the blood stream in the lungs, kidneys and liver.

Although coated microbubbles can survive in the body for an extended period, they can also be selectively destroyed. More specifically, at moderately high sound pressure amplitudes, acoustic pressure waves can cause the shells of coated microbubbles to rupture, freeing the bubbles to behave as non-coated microbubbles by quickly diffusing into the bloodstream. U.S. Pat. No. 5,813,613 to Averkiou, et al., which is incorporated herein by reference, discloses a technique for using the destruction of microbubbles as described above to provide a measure of tissue perfusion. Basically, the Averkiou, et al. technique involves transmitting a high intensity ultrasonic pulse to a selected sample volume in the body, thereby destroying the microbubbles at that location. After the microbubbles in the sample volume have been destroyed, the blood that contained the destroyed microbubbles flows out of tissues at that location, and new blood containing microbubbles reperfuses these tissues. After a given period of reperfusion another high intensity pulse is transmitted with the received echoes indicating the microbubble concentration at the sample volume after the given period of reperfusion. This pulse destroys the microbubbles a second time, and a different reperfusion period is allowed to pass and another high intensity pulse transmitted to determine the microbubble concentration after the different period of reperfusion. The cycle is repeated for a plurality of reperfusion period and the measurements thus taken are plotted to produce a reperfusion curve showing the rate of reperfusion of the tissue at the sample volume.

While this technique is effective for measuring the perfusion rate and producing a reperfusion curve for a specific sample volume, it would be desirable to be able to make and display the results of perfusion measurements for a large region of tissue and not just a particular sample volume location. Such a capability would enable the rapid diagnosis the perfusion rate of a significant region of tissue such as the myocardium, enabling the clinician to quickly identify small regions of tissue where perfusion is problematic due to ischemia or other bloodflow conditions.

SUMMARY OF THE INVENTION

A method and system displays a parametric contrast image of the perfusion rate of anatomy in an image, depicting the rate of reperfusion for a significant area or volume of tissue in the body simultaneously. A single static parametric perfusion image may be produced, or a sequence of parametric perfusion images produced to illustrate changes in the perfusion rate over time. Ungated or gated images may be used, enabling the parametric display to be keyed to specific phases of the heart cycle. Multiple parameters can be combined in a single parametric image, if desired. The inventive technique may be used with bolus contrast injections or with a continuous infusion of the contrast agent.

DETAILED DESCRIPTION OF THE INVENTION

Figure 1:
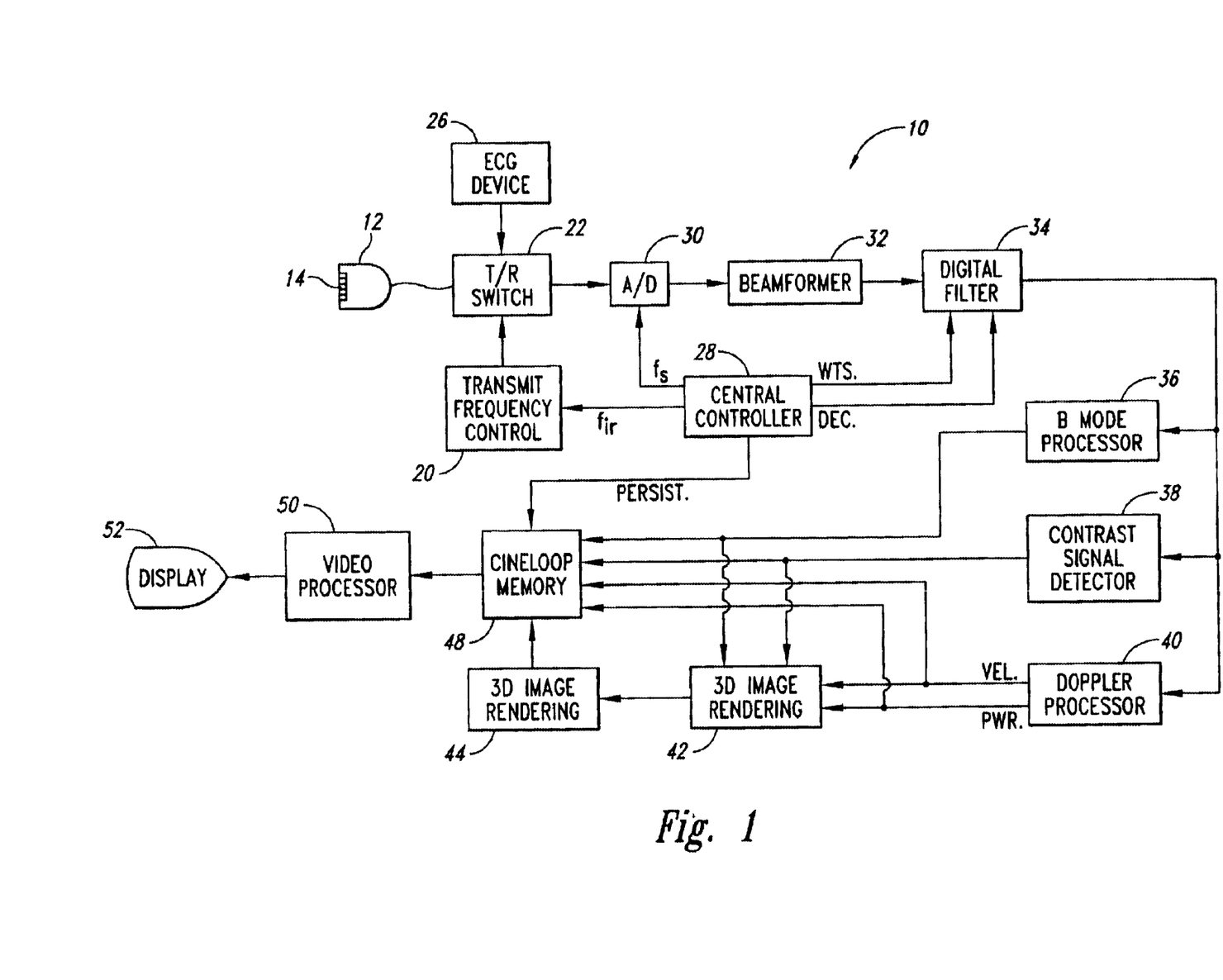
FIG. 1 is a block diagram of an ultrasonic imaging system according to one embodiment of the invention.

An ultrasonic diagnostic system 10 constructed in accordance with the principles of the present invention is shown in FIG. 1. An ultrasonic scanhead 12 includes an array 14 of ultrasonic transducers that transmit and receive ultrasonic pulses. The array may be a one dimensional linear or curved array for two dimensional imaging, or may be a two dimensional matrix of transducer elements for electronic beam steering in three dimensions. The ultrasonic transducers in the array 14 transmit ultrasonic energy and receive echoes returned in response to this transmission. A transmit frequency control circuit 20 controls the transmission of ultrasonic energy at a desired frequency or band of frequencies through a transmit/receive ("T/R") switch 22 coupled to the ultrasonic transducers in the array 14. The times at which the transducer array is activated to transmit signals may be synchronized to an internal system clock (not shown), or they may be synchronized to a bodily function such as the heart cycle, for which a heart cycle waveform is provided by an ECG device 26. As explained in greater detail below, when the heartbeat is at the desired phase of its cycle as determined by the waveform provided by ECG device 26, the scanhead is commanded to transmit an ultrasound beam. The ultrasonic energy transmitted by the scanhead 12 can be relatively high energy (high mechanical index or MI) which destroys or disrupts contrast agent in the image field, or it can be relatively low energy which enables the return of echoes from the contrast agent without substantially disrupting it. The frequency and bandwidth of the ultrasonic energy generated by the transmit frequency control circuit 20 is controlled by a control signal $f_{tr}$ generated by a central controller 28.

Echoes of the transmitted ultrasonic energy are received by the transducers in the array 14, which generates echo signals that are coupled through the T/R switch 22 and digitized by analog to digital ("A/D") converters 30. The A/D converters 30 sample the received echo signals at a sampling frequency controlled by a $f_s$ signal generated by the central controller 28. The desired sampling rate dictated by sampling theory is at least twice the highest frequency of the received passband, and might be on the order of at least 30–40 MHz. Sampling rates higher than the minimum requirement are also desirable.

The echo signal samples from the individual transducers in the array 14 are delayed and summed by a beamformer 32 to form coherent echo signals. The digital coherent echo signals are then filtered by a digital filter 34. In this embodiment, the transmit frequency and the receiver frequency are individually controlled so that the beamformer 32 is free to receive a band of frequencies which is separate from the transmitted band. The digital filter 34 bandpass filters the signals, and can also shift the frequency band to a lower or baseband frequency range. The digital filter could be a filter of the type disclosed in U.S. Pat. No. 5,833,613.

Filtered echo signals from tissue are coupled from the digital filter 34 to a B mode processor 36 for conventional B mode processing. The B mode image may be created from echoes returning from nondestructive ultrasonic imaging pulses. As discussed above, pulses of low amplitude, high frequency, and short burst duration will generally not destroy the microbubbles.

Filtered echo signals of a contrast agent, such as microbubbles, are coupled to a contrast signal detector 38. The contrast signal detector 38 preferably separates echoes returned from harmonic contrast agents by the pulse inversion technique, in which echoes resulting from the transmission of multiple pulses to an image location are combined to cancel fundamental signal components and enhance harmonic components. A preferred pulse inversion technique is described in U.S. Pat. No. 6,186,950, for instance, which is hereby incorporated by reference. The detection and imaging of harmonic contrast signals at low MI is described in U.S. Pat. No. 6,171,246, the contents of which is also incorporated herein by reference.

The filtered echo signals from the digital filter 34 are also coupled to a Doppler processor 40 for conventional Doppler processing to produce velocity and power Doppler signals. The outputs of these processors may be displayed as planar image, and are also coupled to a 3D image rendering processor 42 for the rendering of three dimensional images, which are stored in a 3D image memory 44. Three dimensional rendering may be performed as described in U.S. Pat. No. 5,720,291, and in U.S. Pat. Nos. 5,474,073 and 5,485,842, all of which are incorporated herein by reference.

The signals from the contrast signal detector 38, the processors 36 and 40, and the three dimensional image signals from the 3D image memory 44 are coupled to a Cineloop® memory 48, which stores image data for each of a large number of ultrasonic images, as explained in greater detail below. The image data are preferably stored in the Cineloop memory 48 in sets, with each set of image data corresponding to an image obtained at a respective time. The sets of image data for images obtained at the same time during each of a plurality of heartbeats are preferably stored in the Cineloop memory 48 in the same group. Thus, as explained below, the image data in a group can be used to display a parametric image showing tissue perfusion at a respective time during the heartbeat. The groups of image data stored in the Cineloop memory 48 are coupled to a video processor 50, which generates corresponding video signals for presentation on a display 52. The video processor 50 preferably includes persistence processing, whereby momentary intensity peaks of detected contrast agents can be sustained in the image, such as described in U.S. Pat. No. 5,215,094, which is also incorporated herein by reference.

Figure 2:
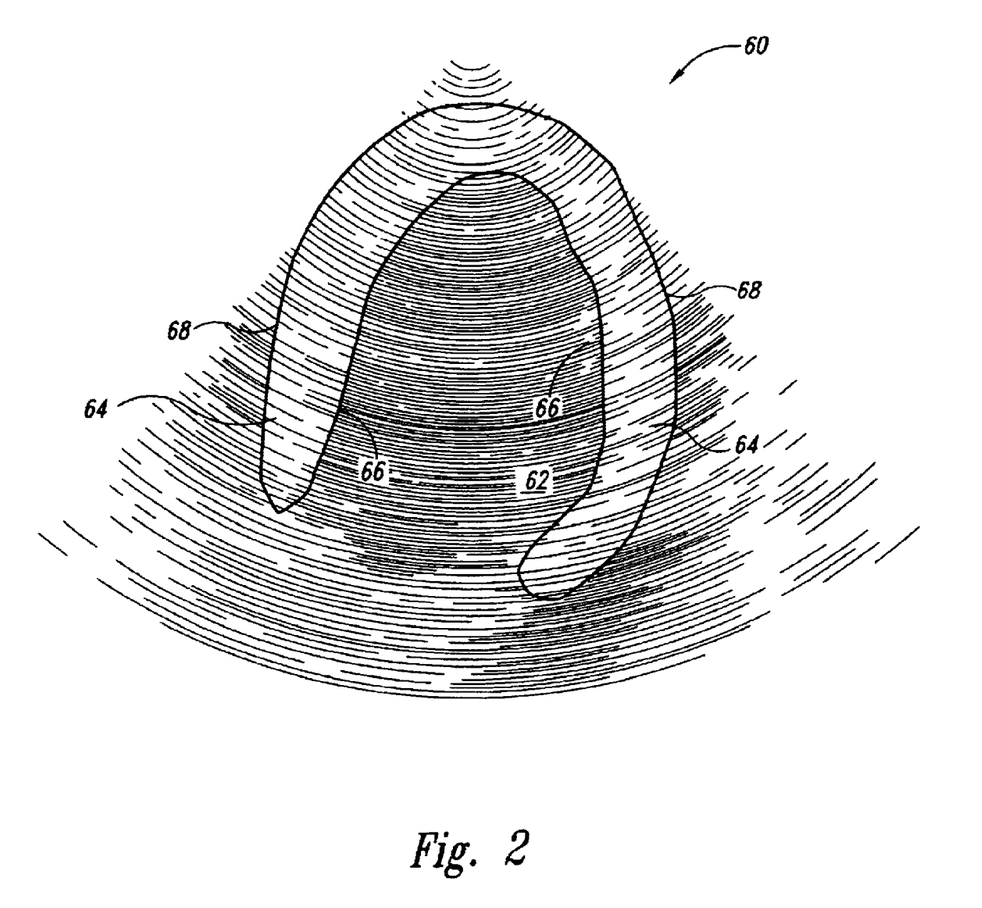
FIG. 2 is a schematic drawing showing a B-mode image of a myocardium obtained using the system of FIG. 1.

The manner in which perfusion can be displayed in a parametric image will now be explained with reference to FIGS. 2–14. An image 60 is obtained from a region of interest, preferably with the aid of the microbubbles used as contrast agents, as shown in FIG. 2. The anatomy shown in FIG. 2 is the left ventricle 62 of a heart, although it will be understood that the region of interest can encompass other tissues or organs. The left ventricle 62 is surrounded by the myocardium 64, which has inner and outer borders, 66, 68, respectively, that defines as an area of interest, the perfused myocardium 64. The myocardium can be distinguished for analysis by segmentation either manually or automatically using conventional or hereinafter developed techniques, as described below.

Figure 3:
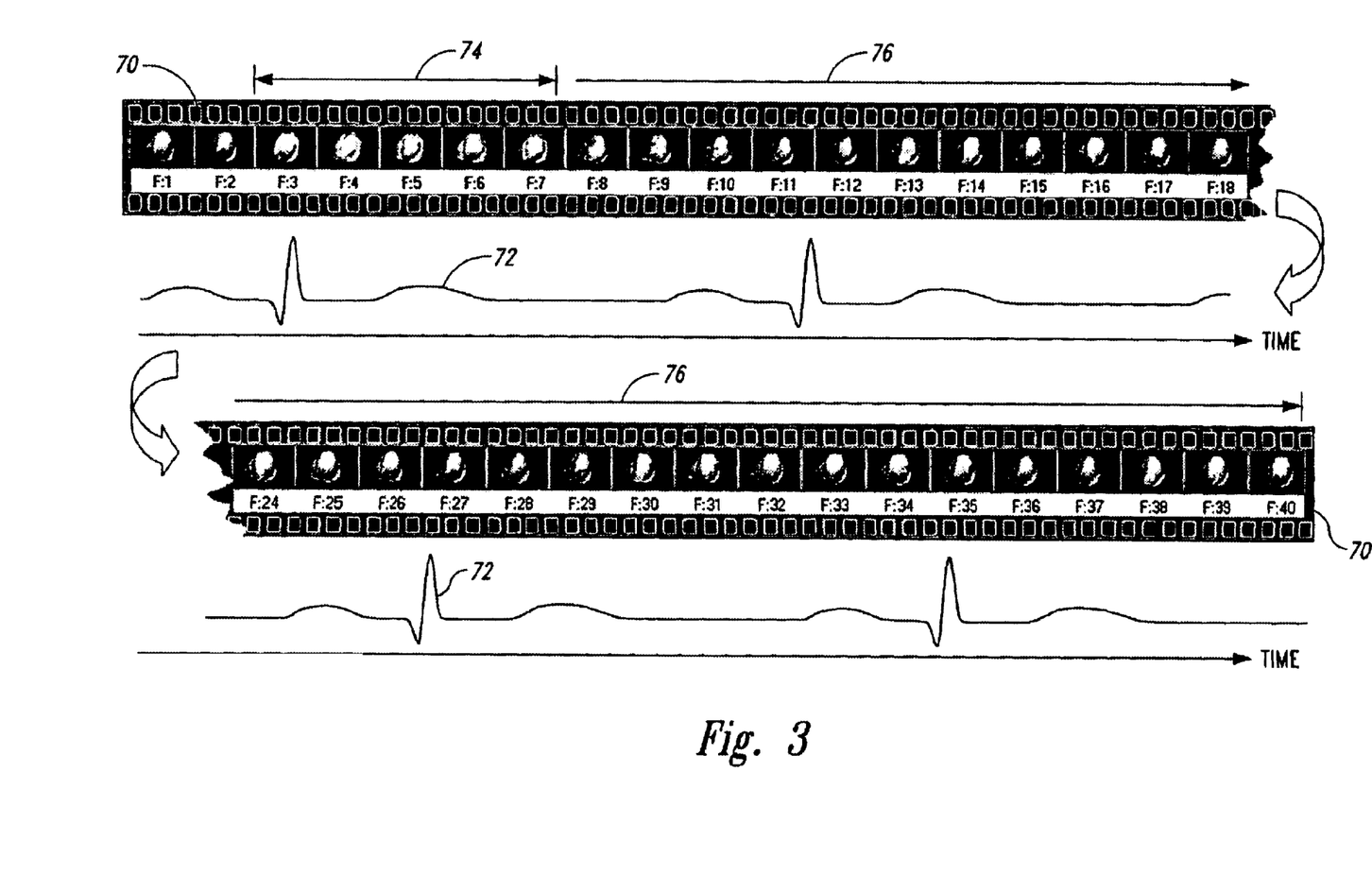
FIG. 3 illustrates the acquisition of a sequence of real time image frames for parametric imaging.

FIG. 3 illustrates a real time sequence 70 of images of the myocardium which have been acquired with a contrast agent present in the heart. The image frames in the sequence are numbered F:1, F:2, F:3, and so on. The sequence is shown in time correspondence to an ECG waveform 72 of the heart cycle. It will be appreciated that during a heart cycle 10, 20, 30, 40 or more images may be acquired, depending upon the heart rate and the ultrasound system frame rate. In one embodiment of the present invention the acquired sequence 70 of images is stored in the Cineloop memory 48. In accordance with the principles of the present invention, during one interval 74 of images, high MI pulses are used to acquire the images. This is typically an interval of 1–10 image frames. The use of the high intensity transmit pulses substantially disrupts or destroys the microbubbles in the image plane or volume. In this discussion these high MI frames are referred to as "flash" frames. At the end of this interval 74 low MI pulses are used to image subsequent image frames over several cardiac cycles delineated by interval 76 as the contrast agent reinfuses the myocardium. The sequence of images shows the dynamics of the cardiac cycle as well as contrast replenishment over many heart cycles.

Figure 4:
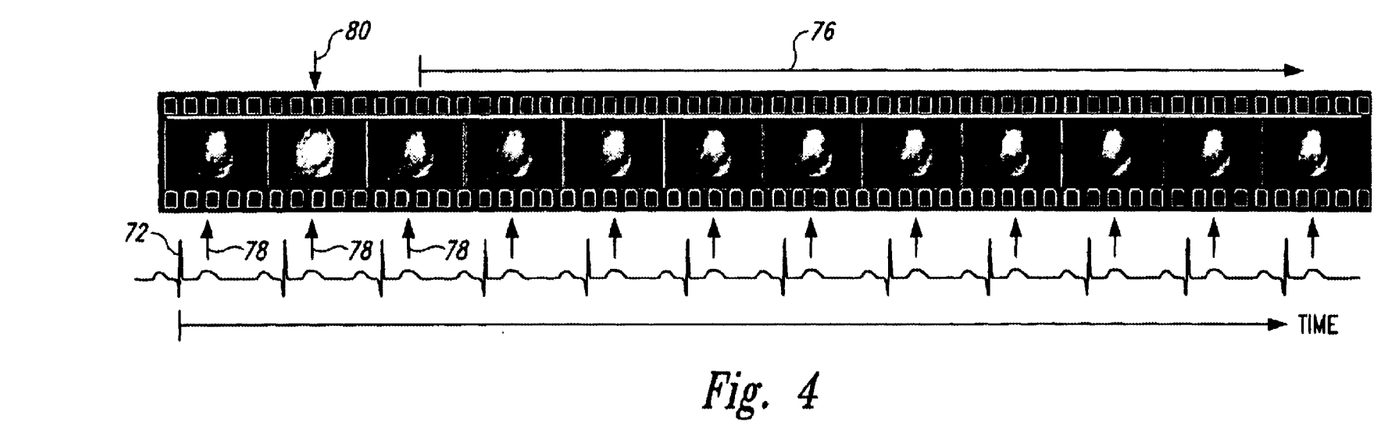
FIGS. 4 illustrates gated (triggered) acquisition of a sequence of frames for parametric imaging.

Instead of acquiring a continual real time sequence of images, images can be selected out of a real time sequence at specific times in the cardiac cycle. FIG. 4 illustrates this triggered acquisition, in which the arrows 78 indicate times triggered from the ECG waveform 72 at which images are acquired at a specific phase of the heart cycle. The arrow 80 indicates the time when one or more flash frames are transmitted, followed by an interval 76 during which low MI images are acquired. In this example only one image is acquired and stored in Cineloop memory during each cardiac cycle. The user sets the trigger timing to determine which part of the cardiac cycle to capture with the triggered images. When these images are replayed from Cineloop memory in real time, they do not show the dynamics of the cardiac cycle, as the heart is at the same phase of the cardiac cycle during each image. The sequence does show contrast replenishment in the triggered images acquired during the low MI interval 76.

Figure 5:
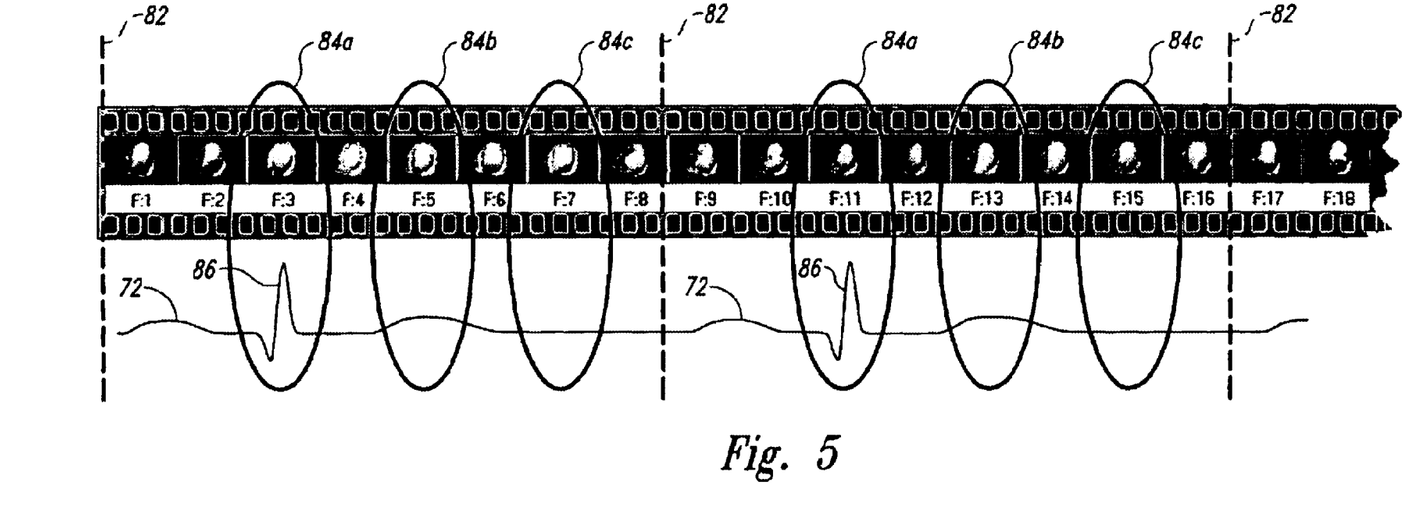
FIG. 5 depicts a sequence of real time images over several heart cycles.
Figure 6A:
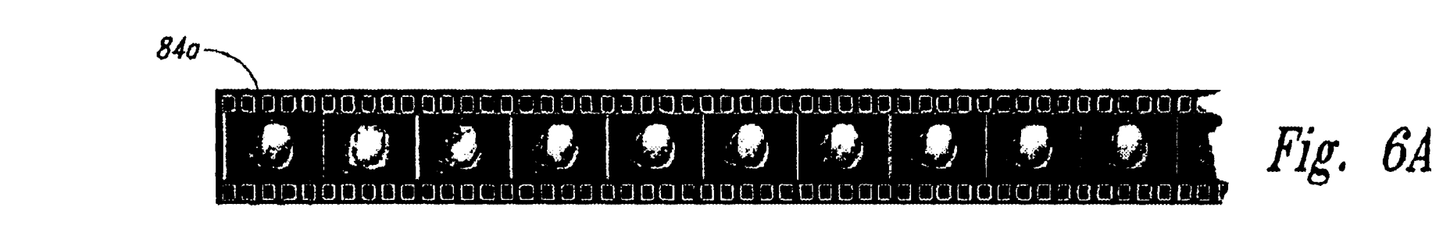
FIGS. 6a, 6b, and 6c illustrate sequences of images for unique phases of the heart cycle assembled from the images of the sequence of FIG. 5.
Figure 6B:
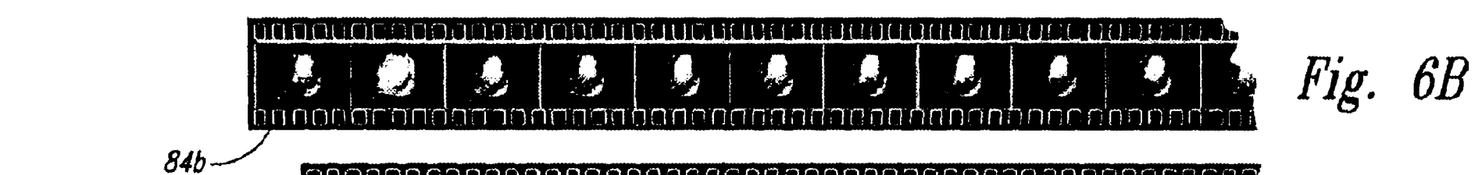
Figure 6C:
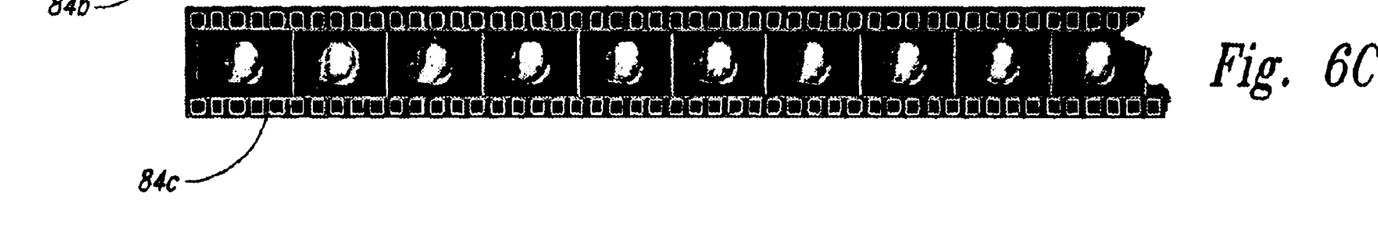

FIGS. 5 and 6a, 6b, and 6c illustrate the assembly of multiple single-phase sequences from a real time continuous acquisition sequence. FIG. 5 illustrates the continuous real time sequence as was shown previously in FIG. 3. The dashed lines 82 represent the divisions between different heart cycles. The illustrated images are low MI images which have been preceded by one or more flash frames (not shown). Circles 84a indicate the time of acquisition triggered by the ECG waveform 72; the image in these circles are seen to be coincident with the QRS waveform 86. These triggered images are assembled in a sequence of images at this phase of the heart, as shown by image sequence 84a in FIG. 6a. In a similar manner, triggered images are selected from the real time sequence at other phases of the heart cycle as shown by circles 84b and 84c. These triggered images are assembled into other sequences of images of their respective heart phases as shown in FIGS. 6b and 6c. This triggering may be done in real time, or in a post-processing operation in which the real time sequence of FIG. 5 is captured in Cineloop memory and the triggered sequences of FIGS. 6a, 6b, and 6c are subsequently assembled from the stored real time sequence.

Figures 7A, 7B, 7C:
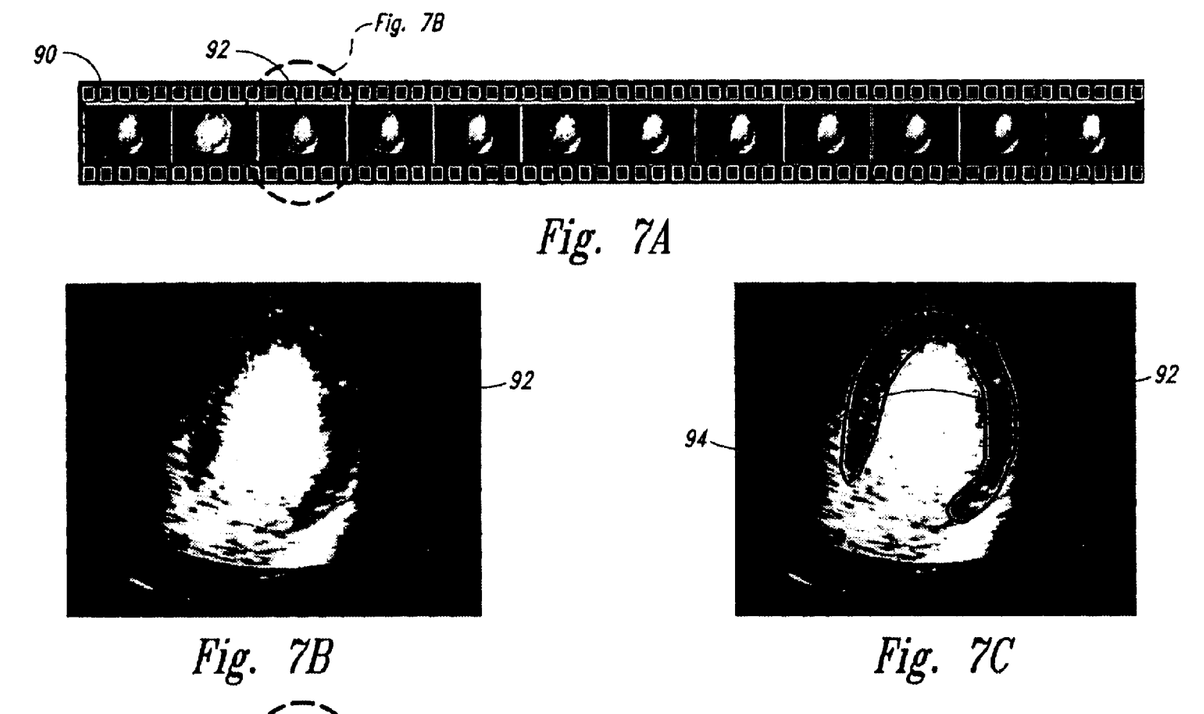
FIGS. 7a–7d illustrate the delineation of a region of interest in an image using assisted border detection.
Figure 7D:
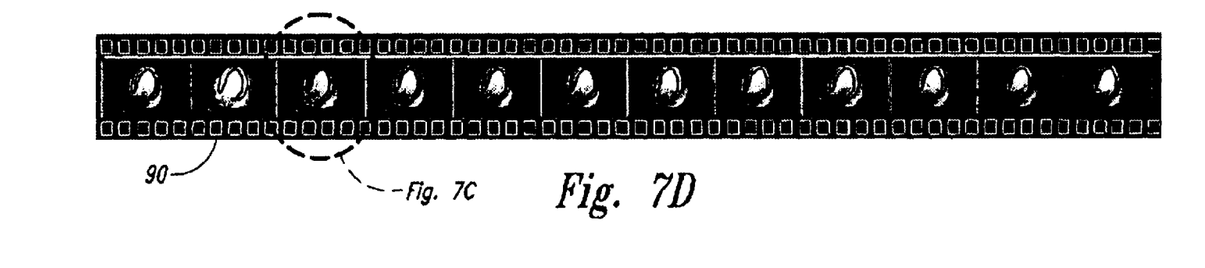
Figure 8A:
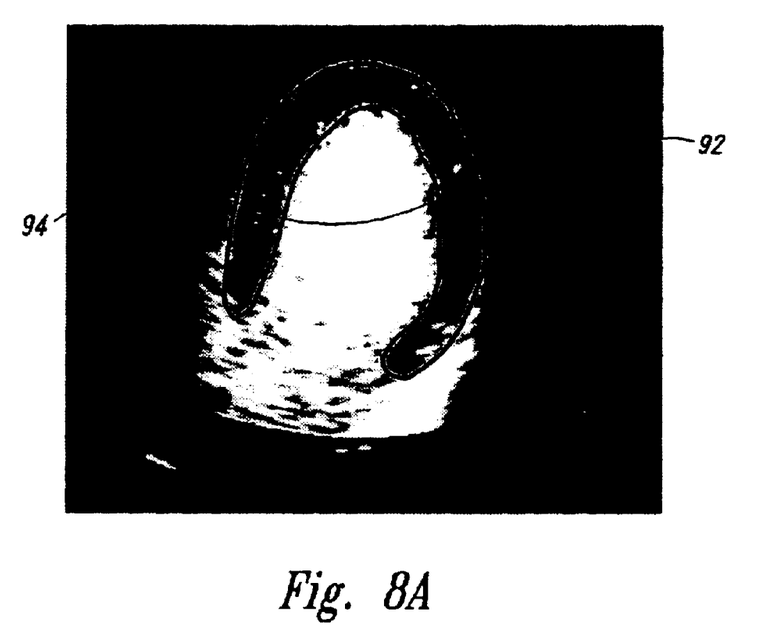
FIGS. 8a and 8b illustrate the masking of a region of interest.
Figure 8B:
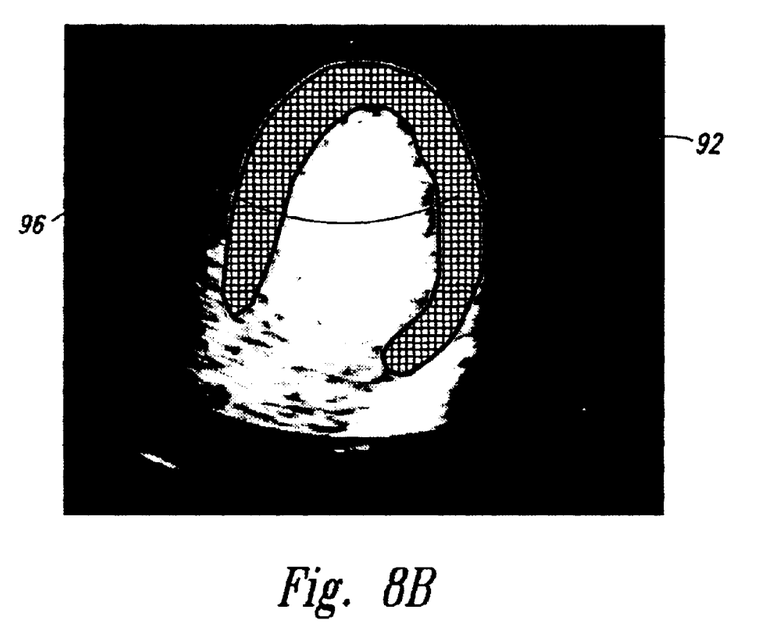

The area of interest in the image, in this example the myocardium, may optionally be delineated by assisted border detection as shown in FIGS. 7a–7d. FIG. 7a illustrates a contrast image sequence 90 which may be a real time sequence 70 or a triggered sequence 80. From the image sequence 90 the user selects an image 92 which shows relatively well defined endocardial and epicardial borders. This image 92 is shown enlarged in FIG. 7b. The selected image is then processed by assisted border detection, as described in U.S. patent [application Ser. No. 09/732,613], entitled "Automated Border Detection in Ultrasonic Diagnostic Images," the contents of which is hereby incorporated by reference. Automated or assisted border detection acts to delineate the myocardium with a border 94 as shown in FIG. 7c. The border outline 94 on the selected image is then used to delineate the border on other images in the sequence 90, as shown in FIG. 7d. Alternatively, the borders may be drawn on the other images in the sequence by processing them individually with the automated border detection algorithm. The area of interest where perfusion is to be represented parametrically is now clearly defined for subsequent processing. If desired, the area of interest may be further defined by a mask 96, as shown in FIG. 8b, in which the area within the border trace is masked. All pixels under the mask are to be processed in this example, while pixels outside of the mask are not processed parametrically.

Figure 9A:
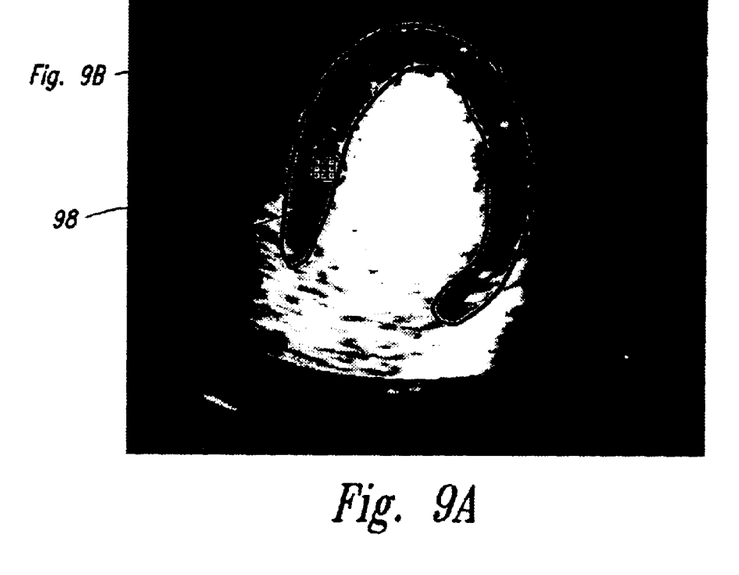
FIGS. 9a and 9b illustrate a preferred technique for quantifying pixel values in a region of interest.
Figures 9B, 10:
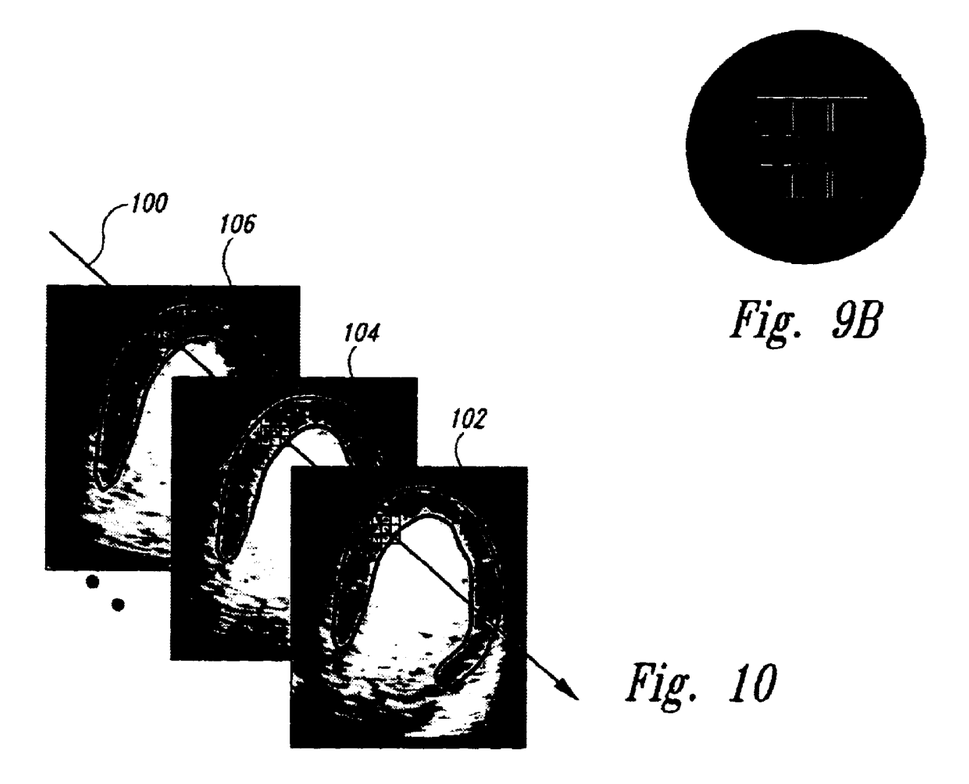
FIG. 10 illustrates the selection of pixel values from a plurality of images for the determination of a perfusion curve for the pixel location.
Figure 11:
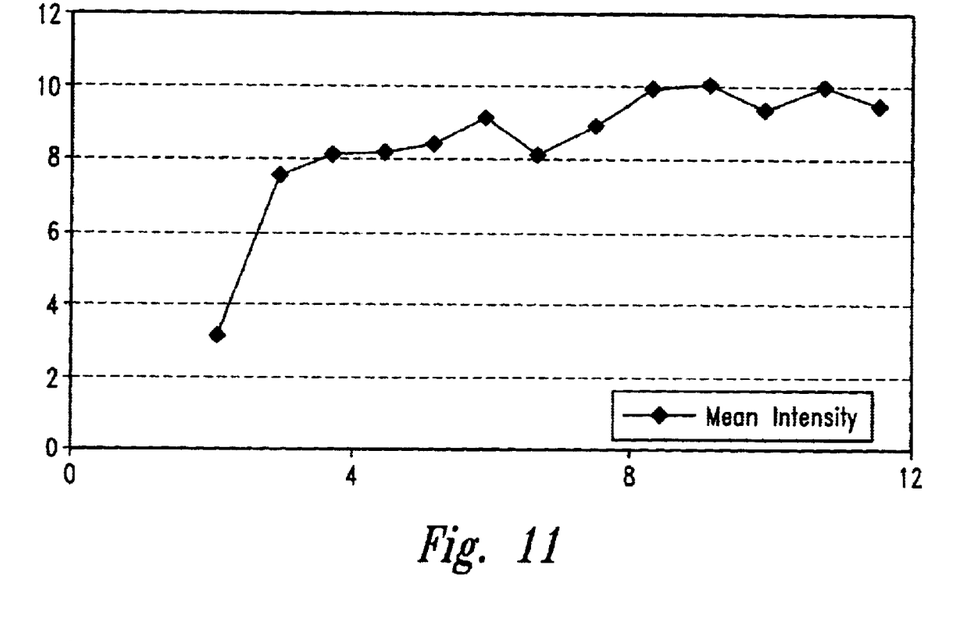
FIG. 11 illustrates the plotting of a perfusion curve from image data.
Figure 12:
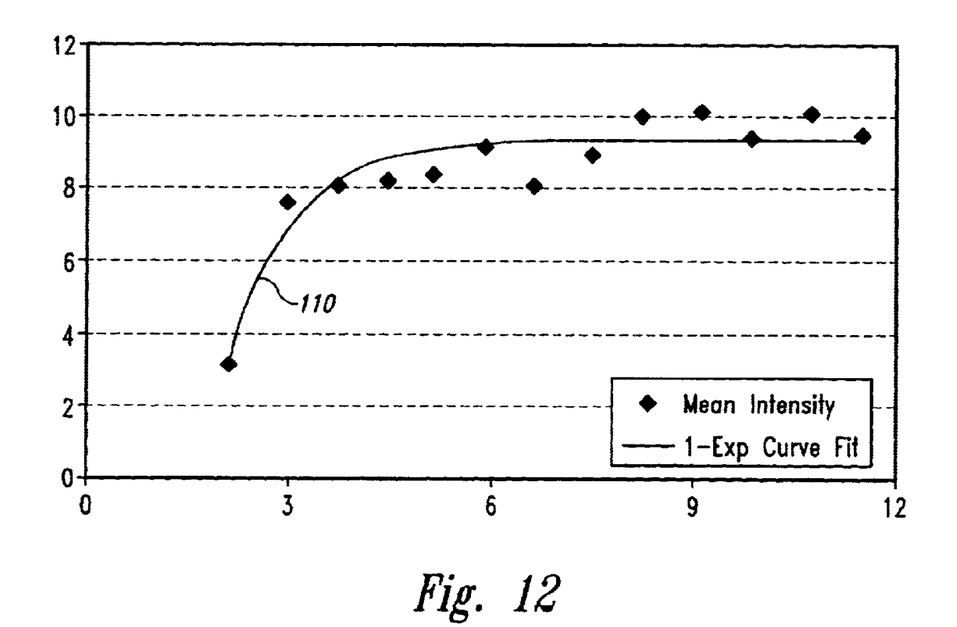
FIG. 12 illustrates the fitting of a smooth curve to the perfusion curve of FIG. 11.

FIGS. 9a and 9b illustrate a preferred technique for processing the pixels within the area of interest. As FIG. 9b shows, for each pixel within the area of interest a mean image intensity value is calculated for a pixel and its surrounding eight neighboring pixels. Pixel values are calculated in this manner for each pixel in the myocardium 98 in this example, and the process is repeated for every pixel in the same location for each image in the sequence as shown for images 102, 104, 106 in FIG. 10. The common location pixel values are, at least conceptually, then plotted graphically as a function of time and mean intensity as shown in FIG. 11, which shows a plot of the common location pixel values intersected by arrow 100 in FIG. 10. The common location pixels are then used to develop a perfusion parameter for display in a two- or three-dimensional image of the area of interest. In a preferred embodiment, parameters are produced by fitting the plotted values to a curve 110 of the form:

$$I(t)=A(1-\exp^{(-B*t)})+C$$

where A is the final curve intensity, B is proportional to the initial slope of the curve, and C is a floating constant. A drawn curve 110 of this form is illustrated in FIG. 12. Parameters may then be formed using the values A, B, and combinations thereof (A*B, A/B, etc.) as shown below.

Figure 13A:
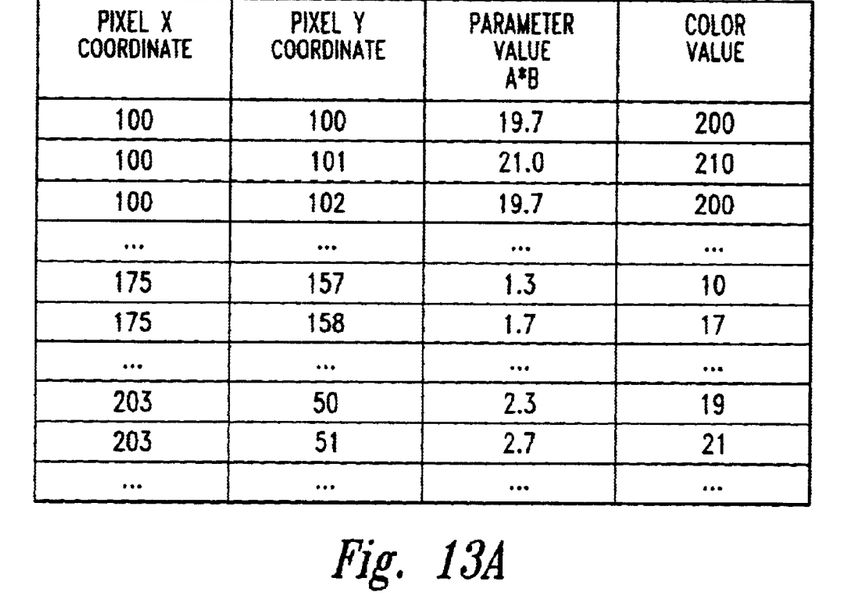
FIGS. 13a and 13b illustrate the mapping of perfusion parameters to a color scale and a two dimensional image.
Figure 13B:
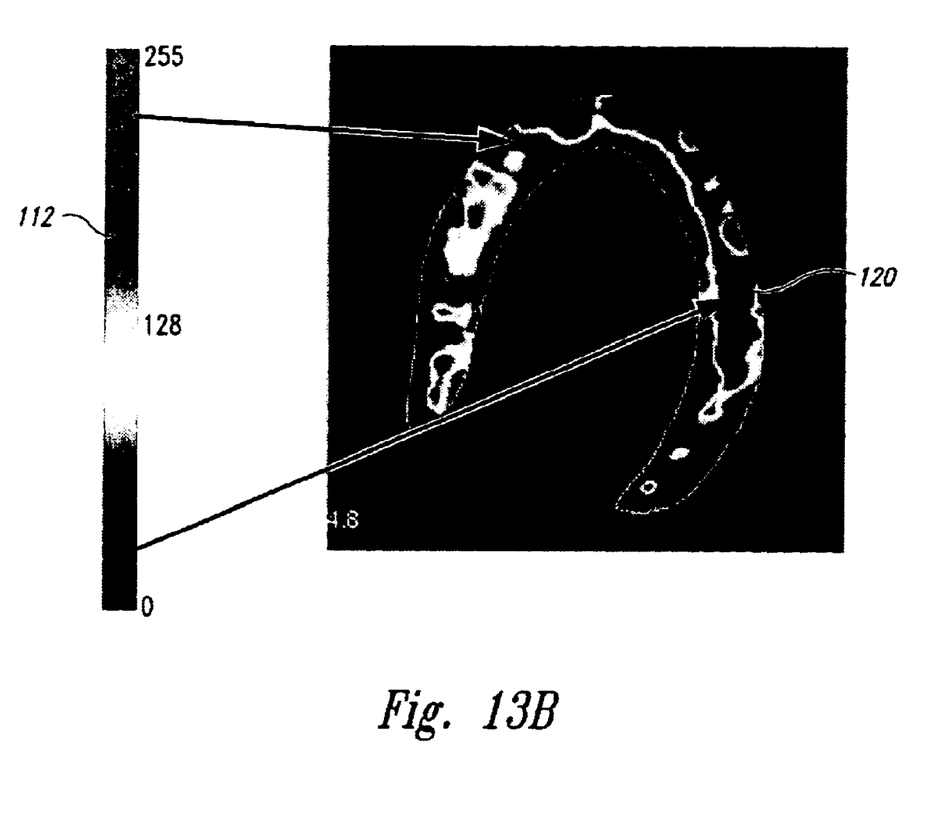

FIGS. 13a–13b illustrate the creation of a parametric image from a parameter value of the form A*B using the curve characteristics described above. In the table of FIG. 13a, the first two columns indicate the locational coordinates of pixels in a two dimensional image. For three dimensional images a third coordinate will be used. The A*B parameter value for each pixel location is represented in the third column. The range of parameter values, represented by the color bar 112 calibrated from zero to 255 between FIGS. 13a and 13b, is then used to encode (map) each parameter value to a color, brightness, or other display characteristic. The colors are then displayed in their respective locations in a two or three dimensional parametric image 120, as shown in FIG. 13b, in which the perfusion of the myocardium of the heart is parametrically displayed.

Figure 14:
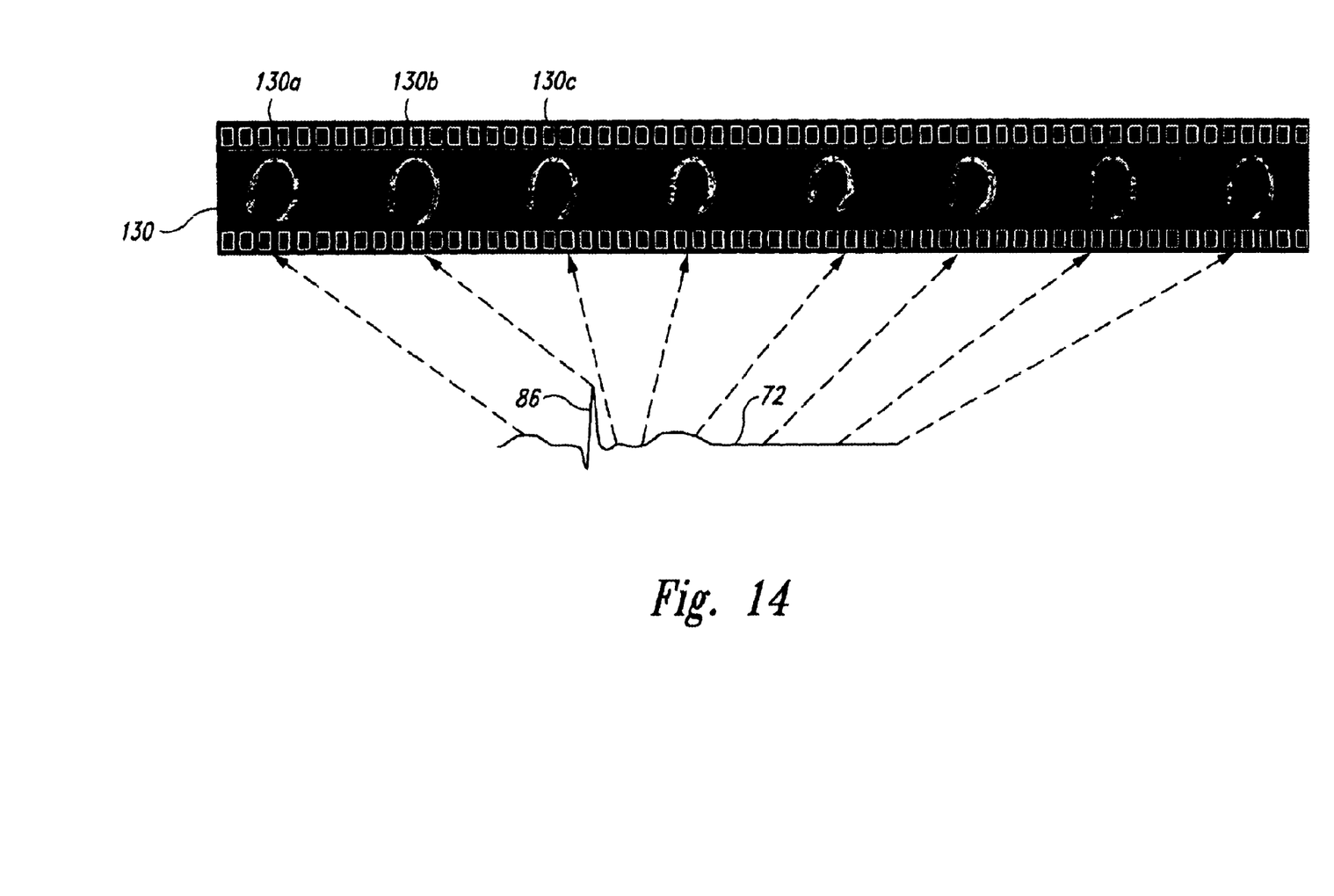
FIG. 14 illustrates a real time display of parametric perfusion images corresponding to different phases of a heart cycle.

The techniques of the present invention may be used to produce a single static image 120 as shown in FIG. 13b, or they may be used to produce a sequence of parametric images which may be displayed in sequence or in real time. For instance, FIG. 14 illustrates a sequence of parametric perfusion images from different phases of the heart cycle, as indicated by the arrows drawn from points on the ECG waveform 72 to individual images in the sequence 130. Each parametric image in the parametric image sequence 130 can be formed by a different one of the different phase sequences of FIGS. 6a, 6b, and 6c, for instance. The images of FIG. 6a are used to produce parametric image 130a, the images of FIG. 6b are used to produce parametric image 130b, and the images of FIG. 6c are used to produce parametric image 130c. When sequence 130 is played in full or partial real time, it will reveal the changing perfusion in the various locations in the myocardium during the different phases of the heart cycle. This image sequence thus reveals both myocardial perfusion information and the dynamics of wall motion of the endocardium in the same diagnostic image sequence.

In organs where perfusion is not as strongly related to the heart cycle, such as perfusion in the liver, kidney, a transplanted organ, or limb of the body, triggering may not be practical and perfusion images will be made during one or more selected reperfusion periods following flash image frames. Parametric images may be used for diagnoses such as tumor detection, where the parameter in the tumor will cause the image to "light up" from reperfusion faster than normal surrounding tissue. Parameters other than that shown for the curve equation given above may be used. For instance, the perfusion parameter could be based upon the error or variance of the actual acquired data (FIG. 11) from a smooth curve such as curve 110. The techniques of the present invention may be used with either bolus injection of the contrast agent, or with continuous infusion of the agent. An example of practice of the present invention with a bolus injection is tumor diagnosis in the liver. Following a bolus injection a tumor in the liver will "light up" as it is infused with the flow of contrast agent from the hepatic arterial blood supply. Normal tissue in the liver lights up at a later time when the bolus of contrast agent enters the liver through the portal vein. At this later time the tumor will appear similar to or less bright than the surrounding normal tissue. Temporal parametric images will reveal these differences in perfusion at the different phases of this diagnostic process.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of providing a parametric ultrasound image of perfusion in a region of interest, comprising:
   perfusing the region of interest with a contrast agent;
   acquiring temporal ultrasonic echo information over a period of time as the region of interest is perfused with the contrast agent;
   identifying temporal echo information corresponding to the acquired temporal ultrasonic echo information at common locations in the region of interest;
   calculating a perfusion parameter from the identified temporal information at each common location; and
   producing a two or three dimensional image of the region of interest in which locations in the region of interest are depicted by the calculated perfusion parameters.

2. The method of claim 1, wherein the act of acquiring comprises flashing the region of interest with high MI ultrasound energy, then acquiring temporal ultrasonic echo information over a period of time with low MI ultrasound energy.

3. The method of claim 2, wherein the act of acquiring comprises acquiring ultrasonic echo information at periodically triggered intervals.

4. The method of claim 1, wherein the act of acquiring comprises acquiring a real time sequence of ultrasonic image information.

5. The method of claim 4, wherein the act of acquiring comprises selecting image information from the real time sequence which relates to a specific phase of bodily activity.

6. The method of claim 1, wherein the act of producing comprises mapping perfusion parameters to a range of display parameters.

7. The method of claim 6, wherein the act of producing comprises mapping perfusion parameters to a range of display colors.

8. The method of claim 1, wherein the act of producing comprises producing a sequence of two or three dimensional parametric images.

9. The method of claim 8, wherein the region of interest comprises the myocardium, wherein producing comprises producing a sequence of parametric images for different phases of a heart cycle,
   wherein the sequence of parametric images depicts both cardiac perfusion characteristics and wall motion.

10. The method of claim 1, wherein the act of identifying further comprises identifying the region of interest by automated border detection.

11. The method of claim 1, wherein the act of calculating a perfusion parameter further comprises fitting a curve to the identified temporal information at each common location and utilizing a characteristic of the curve to calculate the perfusion parameter.

12. The method of claim 1, wherein the act of calculating a perfusion parameter comprises calculating a perfusion parameter for display from at least two other perfusion parameters.

13. An ultrasonic diagnostic imaging system for generating a parametric ultrasonic image of perfusion of blood in tissue in a region of interest, the system comprising:
   a scanhead having an array transducer for scanning a region of interest;
   a beamformer coupled to selectively apply transmit signals of high and low intensity to the transducer and to receive echo signals from the transducer and to generate output signals corresponding thereto;
   a contrast signal detector which acts to identify contrast echo signals;
   a processor coupled to the contrast signal detector and responsive to temporal sequences of contrast echo signals from discrete locations in the region of interest, the processor being operable to develop perfusion parameters relating to the temporal sequences at the discrete locations; and
   a video processor receiving the perfusion parameters and producing image data in which the perfusion parameters are spatially represented.

14. The system of claim 13 wherein the temporal sequences are real time image sequences.

15. The system of claim 13 further comprising a sensor which senses a cyclical bodily function, wherein the temporal sequences are triggered sequences in synchronism with the cyclical bodily function.

16. The system of claim 13 wherein the temporal sequences are acquired in response to low intensity transmit signals and following an interval of high intensity transmit signals.

17. The system of claim 13, wherein the video processor further comprises an automated border detection processor which acts to delineate the region of interest in an ultrasound image.

18. The system of claim 13 wherein the video processor comprises an image processor responsive to the perfusion parameters which acts to map the perfusion parameter values to a display variable.

19. The system of claim 13 wherein the processor is further operable to determine perfusion parameters by fitting temporal contrast echo signals to perfusion curves.

20. The system of claim 15 wherein the sensor comprises a heart cycle sensor, and wherein the video processor acts to produce a sequence of perfusion parametric images relating to phases of a heart cycle.

21. The system of claim 13, wherein the region of interest comprises a volumetric region, and wherein the video processor acts to produce image data for a three dimensional region.

22. A method of providing a parametric ultrasound image of perfusion in a region of interest, comprising:

perfusing the region of interest with a contrast agent;

acquiring temporal ultrasonic echo information over a period of time as the region of interest is perfused with the contrast agent;

identifying temporal echo information corresponding to common locations in the region of interest by identifying the region of interest using automated border detection;

calculating a perfusion parameter from the identified temporal information at each common location; and producing a two or three dimensional image of the region of interest in which locations in the region of interest are depicted by the calculated perfusion parameters.

23. A method of providing a parametric ultrasound image of perfusion in a region of interest, comprising:

perfusing the region of interest with a contrast agent;

acquiring temporal ultrasonic echo information over a period of time as the region of interest is perfused with the contrast agent;

identifying temporal echo information corresponding to common locations in the region of interest;

calculating a perfusion parameter from the identified temporal information at each common location by fitting a curve to the identified temporal information at each common location and utilizing a characteristic of the curve to calculate the perfusion parameter; and producing a two or three dimensional image of the region of interest in which locations in the region of interest are depicted by the calculated perfusion parameters.

24. An ultrasonic diagnostic imaging system for generating a parametric ultrasonic image of perfusion of blood in tissue in a region of interest, the system comprising:

a scanhead having an array transducer for scanning a region of interest;

a beamformer coupled to selectively apply transmit signals of high and low intensity to the transducer and to receive echo signals from the transducer and to generate output signals corresponding thereto;

a contrast signal detector which acts to identify contrast echo signals;

a processor coupled to the contrast signal detector and responsive to temporal sequences of contrast echo signals from discrete locations in the region of interest, the processor being operable to develop perfusion parameters relating to the discrete locations; and a video processor receiving the perfusion parameters and producing image data in which the perfusion parameters are spatially represented, the video processor including an automated border detection processor which acts to delineate the region of interest in an ultrasound image.

* * * * *